United States Patent [19]

Martin et al.

[11] Patent Number: 5,263,484
[45] Date of Patent: Nov. 23, 1993

[54] METHOD OF DETERMINING WHICH PORTION OF A STRESS SENSOR IS BEST POSITIONED FOR USE IN DETERMINING INTRA-ARTERIAL BLOOD PRESSURE

[75] Inventors: Stephen A. Martin, Carlsbad; Robert D. Butterfield, Poway, both of Calif.

[73] Assignee: IVAC Corporation, San Diego, Calif.

[21] Appl. No.: 835,634

[22] Filed: Feb. 13, 1992

[51] Int. Cl.$^5$ ............................................. A61B 5/02
[52] U.S. Cl. .................................. 128/672; 128/677
[58] Field of Search ................ 128/672, 677, 687–690, 128/668, 748

[56] References Cited

U.S. PATENT DOCUMENTS

| | | |
|---|---|---|
| 4,269,193 | 5/1981 | Eckerle . |
| 4,802,488 | 2/1989 | Eckerle . |
| 4,893,631 | 1/1990 | Wenzel et al. . |
| 5,158,091 | 10/1992 | Butterfield et al. ................ 128/748 |

*Primary Examiner*—Lee S. Cohen
*Assistant Examiner*—Samuel Gilbert
*Attorney, Agent, or Firm*—Dykema Gossett

[57] ABSTRACT

A method, for use in a non-invasive blood pressure monitoring system, of determining which portion of a stress sensitive element of a tissue stress sensor is best located for detecting the stress of tissue overlying an artery of interest. The tissue stress sensor is placed in communication with tissue overlying the artery of interest and a plurality of electrical signals are obtained therefrom representing stress data across the length of the stress sensitive element. Each electrical signal represents stress datum communicated to a predetermined portion of the stress sensitive element. From the stress datum, a centroid of energy is computed and the centroid of energy is used to determine which portion of the stress sensitive element is best located for determining the blood pressure within the artery of interest. A second method is disclosed which uses the centroid of a tissue foundation flexibility function to determine the best location along the stress sensitive element for determining blood pressure.

39 Claims, 7 Drawing Sheets

METHOD OF DETERMINING WHICH PORTION OF A STRESS SENSOR IS BEST POSITIONED FOR USE IN DETERMINING INTRA-ARTERIAL BLOOD PRESSURE

TECHNICAL FIELD

The present invention generally relates to pressure measurement systems, and more particularly relates to a method for non-invasively determining the intra-arterial blood pressure of a wearer.

BACKGROUND OF THE INVENTION

Systems for measuring the intra-arterial blood pressure of a patient can be subdivided into two main groups—those which invade the arterial wall to access blood pressure and those which use non-invasive techniques. Traditionally, the most accurate blood pressure measurements were achievable only by using invasive methods. One common invasive method involves inserting a fluid filled catheter into the patient's artery.

While invasive methods provide accurate blood pressure measurements, the associated risk of infection and potential for complications, in many cases, outweigh the advantages in using invasive methods. Because of these risks associated with invasive methods, a non-invasive method, known as the Korotkoff method is widely used.

The Korotkoff method is known as an auscultatory method because it uses the characteristic sound made as the blood flows through the artery to mark the points of highest (systolic) and lowest (diastolic) blood pressure. Although the Korotkoff method is non-invasive, it only provides a measurement of the highest pressure point and the lowest pressure point along the continuous pressure wave. While systolic and diastolic pressure are sufficient for accurate diagnosis in many instances, there are many applications in which it is desirable to monitor and utilize the entire characteristic curve of the blood pressure wave. In these applications, the Korotkoff method is simply incapable of providing ample information. In addition to this limitation of the Korotkoff method, it necessitates the temporary occlusion (complete closing) of the artery in which blood pressure is being monitored. While arterial occlusion is not prohibitive in many applications, there are occasions where the patient's blood pressure must be monitored continuously (such as when undergoing surgery) and accordingly, the prohibiting of blood flow, even on a temporary basis, is undesirable.

Because of the above-mentioned risks involved with invasive blood pressure measurement, and the shortcomings of the Korotkoff method, extensive investigation has been conducted in the area of continuous, non-invasive blood pressure monitoring and recording. Some of these non-invasive techniques make use of tonometric principles which take advantage of the fact that as blood pressure flows through the arterial vessel, forces are transmitted through the artery wall and through the surrounding arterial tissue and are accessible for monitoring at the surface of the tissue. Because the tonometric method of measuring blood pressure is non-invasive, it is used without the risks associated with invasive techniques. Furthermore, in addition to being more accurate than the Korotkoff method discussed above, it has the capability of reproducing the entire blood pressure wave form, as opposed to only the limited systolic and diastolic pressure points provided by the Korotkoff method.

Because the accuracy of tonometric measurements depend heavily upon the method and apparatus used to sense tissue forces, several sensors have been specifically developed for this purpose. For example, U.S. Pat. No. 4,423,738 issued to Newgard on Jan. 3, 1984 discloses an electromechanical force sensor which is made up of an array of individual force sensing elements, each of which has at least one dimension smaller than the lumen of the underlying artery wherein blood pressure is to be measured. Also, U.S. Pat. No. 4,802,488 issued to Eckerle on Feb. 7, 1989, discloses an electromechanical transducer that includes an array of transducer elements. The transducer elements extend across an artery with transducer elements at the ends of the array extending beyond opposite edges of the artery. Additionally, U.S. patent application Ser. Nos. 07/500,063 and 07/621,165 both disclose tonometric sensors for use in determining intra-arterial blood pressure. Each of the above four mentioned patents/patent applications disclose transducers having sensing portions that span well beyond the lumen opening of the underlying artery. One main reason it is advantageous to construct a sensor in this manner is because the arteries of interest are relatively small and difficult to locate. By constructing tonometric sensors which employ a relatively long sensing area, the placement of the sensor by a technician, is not as critical as it would be if the sensor was capable of only sensing along a narrow region.

Although by constructing a tonometric sensor with a long sensing portion, the technician's task is simplified, it introduces certain complexities into the methodology used for determining intra-arterial blood pressure. For example, because the sensor face is made relatively long as compared to the lumen of the underlying artery, only a small fraction of the sensing portion of the tissue stress sensor is overlying the artery, and it is only this portion which is sensing useful forces (i.e. forces which are related to intra-arterial blood pressure). The remaining portion of the sensing portion is in contact with tissue which does not overlie the artery of interest, and accordingly, does not transmit forces to the sensing portion which can be used for determining intra-arterial pressure.

Therefore, in view of the above complexities, when employing tonometric sensors of the type discussed above, before the accurate intra-arterial blood pressure can be determined, a method must be employed for determining which portion of the sensor is best positioned over the artery of interest for determining the intra-arterial blood pressure. One such method is disclosed in U.S. Pat. No. 4,269,193 issued to Eckerle on May 26, 1981. The method disclosed in the '193 patent includes selecting the transducer element which has a maximum pulse amplitude output and then looking to its neighbors and choosing the neighbor having a spacially local minimum of at least one of the diastolic and systolic pressures. Other methods are disclosed in U.S. Pat. No. 4,802,488 issued to Eckerle on Feb. 7, 1989. In the '488 patent the following methods are disclosed, a curve-fit method, a two-humps method, a center-of-gravity method, and a "catch-all" method which includes using one of the three aforementioned methods in conjunction with externally supplied user information (such as sex, height, age, etc.). Also, in U.S. Pat. No. 4,893,631 issued to Wenzel, et al. on Jan. 16, 1990, discloses a method for determining which sensor in an array of sensors best tracks the pulse in an underlying artery using a spacially weighted averaging method. This method employs the steps of finding local diastolic pressure minimums, selecting the number of transducers spanning the local minimums, computing the spacially weighted average from elements centered about the local minimums and computing a weighted average therefrom.

Although the above-referenced methods may yield some degree of success, the Applicants of the present invention believe that a method which is superior to those heretofore disclosed methods employs the use of stress energy. For example, it is believed, that the area of the sensor which is best positioned to determine intra-arterial pressure is that portion which receives the greatest contact stress energy from the tissue overlying the artery of interest.

In addition to the above-referenced contact stress energy transfer methodology, a second methodology is disclosed which uses a tissue flexibility distribution method to determine which portion of the stress sensitive element is best suited to measure intra arterial blood pressure. This approach is based on the idea that the tissue immediately over the artery of interest is more flexible than the tissue remote from the artery of interest. By employing a method which determines the flexibility of the tissue at each portion along the stress sensitive element, it can be determined which portion of the stress sensitive element is best suited to use in computing intra-arterial pressure.

Thus, it is an object of this invention to provide a method for determining which portion of a stress sensitive element is best suited to determine intra-arterial blood pressure.

Two methods are disclosed for achieving this object. The first method includes determining which portion along the length of the stress sensitive element receives maximum energy transfer from the tissue overlying the artery of interest. The second method involves determining which portion of the tissue overlying the artery of interest is most flexible.

By determining which portion of the stress sensitive element receives the greatest energy transfer or by determining which portion of the tissue underlying the stress sensitive element is most flexible, this information can be used to determine which portion of the stress sensing element is best suited for determining intra-arterial blood pressure of an underlying artery.

SUMMARY OF THE INVENTION

In light of the foregoing objects, the present invention provides a method, for use in non-invasive blood pressure monitoring, of determining which portion of a stress sensitive element of a tissue stress sensor is best located for detecting the stress of tissue overlying an artery of interest, the stress sensitive element having a length that exceeds the lumen of the artery of interest, the method generally including the steps of; placing the stress sensitive element of the tissue stress sensor in communication with the tissue overlying the artery of interest, and orienting the tissue stress sensitive element such that the tissue stress sensitive element spans beyond the lumen of the artery of interest; obtaining from the tissue stress sensor at least one electrical signal representing stress data across the length of the stress sensitive element, said stress data including stress datum communicated to a predetermined portion of the stress sensitive element from the tissue overlying the artery of interest, each predetermined portion of the stress sensitive element lying along the length of the stress sensitive element; computing from the stress data, a centroid of energy associated with the stress sensitive element; and using the centroid of energy to determine which portion of the stress sensitive element is best located for determining the blood pressure within the artery of interest.

In a preferred embodiment, the stress data includes data which corresponds to the systolic blood pressure, diastolic blood pressure, pulsatile blood pressure, or the mean pressure within the artery of interest.

In a preferred embodiment, the disclosed method includes using each stress datum value to calculate a corresponding energy value, each energy value being associated with one predetermined portion of the stress sensitive element, and determining which one of the energy values is a maximum, and calculating the centroid of energy using only stress datum values which have an energy value which exceeds a predetermined percentage of the maximum energy value.

In a further preferred embodiment, the method of the present invention includes using each stress datum value to calculate a corresponding energy value, each energy value being associated with one of the predetermined portions of the stress sensitive element, ordering the energy values according the their respective magnitudes and calculating the centroid of energy by using only stress datum values associated with a first n energy values of highest magnitude. Preferably, n is determined by associating each energy value ordered with a predetermined segment length along the length of the stress sensitive element, selecting the energy values of greatest magnitude and totaling the predetermined segment lengths associated with all of the selected energy values, and setting n equal to the number of energy values selected when the cumulative predetermined segment lengths exceed a predetermined percentage of the length of the stress sensitive element.

A further preferred embodiment of the disclosed method includes using each of the stress datum values to calculate a corresponding energy value, each of the energy values being associated with a predetermined portion of the stress sensitive element, and attaching a weighing factor to each one of the energy values and calculating the centroid of energy using the weighted energy values.

A second method is disclosed for use in a non-invasive blood pressure monitoring system, of determining which portion of a stress sensitive element of a tissue stress sensor is best located along the length of the stress sensitive element for detecting the stress of tissue overlying an artery of interest, the length of the stress sensitive element exceeding the lumen of the artery of interest, the method including the steps of placing the stress sensitive element of the tissue stress sensor in communication with the tissue overlying the artery of interest, and orienting the stress sensitive element such that the stress sensitive element spans beyond the lumen of the artery of interest; causing the stress sensitive element to act against the tissue overlying the artery of interest thereby causing in the artery a first applanation state and obtaining an index of the first artery applanation state; obtaining, during the first applanation state, from the tissue stress sensor at least one electrical signal representing a first set of stress data across the length of the stress sensitive element, said at least one signal representing stress datum communicated to a predetermined portion of the stress sensitive element from the tissue overlying the artery of interest, each predetermined portion of the stress sensitive element lying along the length of the stress sensitive element; causing the stress sensitive element to act against the tissue overlying the artery of interest thereby causing in the artery, a second artery applanation state, and obtaining an index of the second artery applanation state; obtaining, during the second artery applanation state, from the tissue stress sensor, a plurality of electrical signals representing a second set of stress data across the length of the stress sensitive element, each signal of the plurality of electrical signals representing stress datum communicated to one of the predetermined portions of the stress sensitive element from the tissue overlying the artery of interest; using the first and second sets of stress data and the first and second artery applanation state indexes to construct tissue flexibility data values which define a tissue flexibility function relating the flexibility of the tissue overlying the artery of interest to x, where x is a location along the length of the stress sensitive element; computing, using the tissue flexibility data values, a centroid of tissue flexibility; and using the centroid of tissue flexibility to determine which portion of the stress sensitive element is best located for determining the blood pressure within the artery of interest.

In a preferred embodiment, the first and second sets of stress data include using the data corresponding to the diastolic blood pressure, systolic blood pressure, pulsatile blood pressure, or mean blood pressure within the artery of interest.

Other advantages and meritorious features of the present invention will become more fully understood from the following description of the preferred embodiments, the appended claims, and the drawings, a brief description of which follows.

DETAILED DESCRIPTION OF THE PREFERRED EMBODIMENTS

Figure 1:
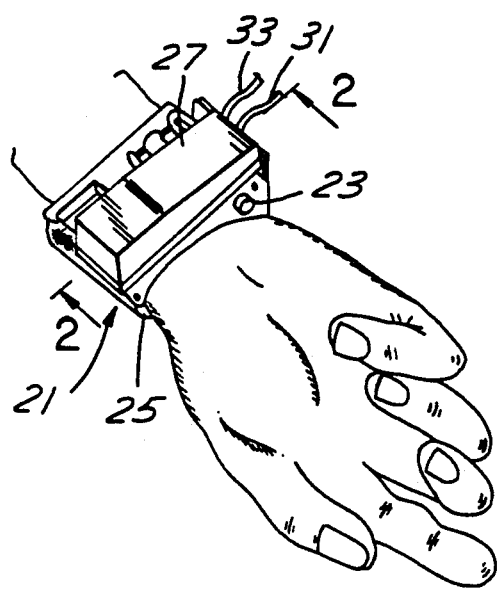
FIG. 1 is a perspective view of a tissue stress sensor attached to the wrist of a wearer.

Now referring to FIG. 1, wrist mount apparatus 21 includes base 23 and flexible strap 25. Flexible strap 25 is adapted to engage base 23 to the wrist of a user. Tissue stress sensor housing 27 is fastened to base 23 and houses a tissue stress sensor for transducer) 20 (tissue stress sensor not shown) and a means 29 for moving the tissue stress sensor 20 (see FIG. 2) into operative engagement with the tissue overlying an artery of interest. Various electrical signals are derived from the tissue stress sensor located within sensor housing 27 and are made available therefrom via conductors within cable 31. These electrical signals carry data which will be used to derive the intra-arterial blood pressure of the wearer of apparatus 21.

Figure 2:
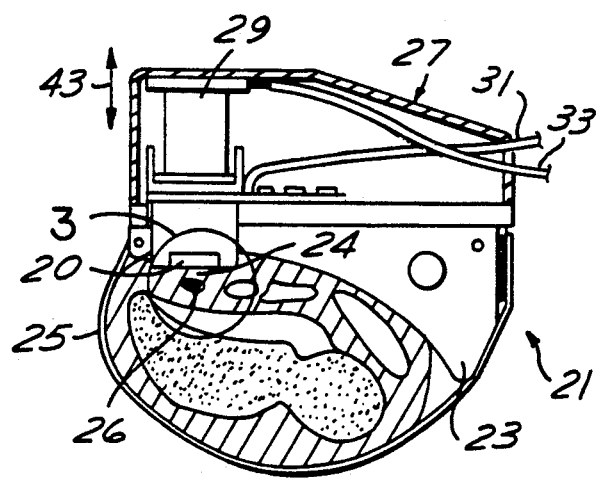
FIG. 2 is a cross sectional view taken substantially along lines 2—2 of FIG. 1.

Now referring to FIG. 2, sensor housing 27 is mounted to base 23. Within sensor housing 27 is mounted a fluid operated slave bellows 29. Bellows 29 is attached to, at one of its ends tissue stress sensor 20. As bellows 29 receives a displacement fluid from a source of fluid via tubing 33, it expands downwardly 43 thereby causing tissue stress sensor 20 to engage tissue 24 overlying artery of interest 26.

Figure 3:
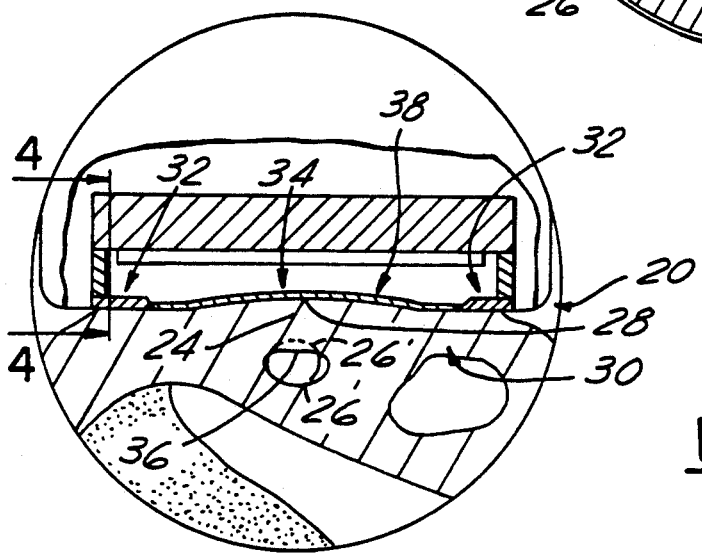
FIG. 3 is an enlarged view of encircled portion 3 of FIG. 2.

Now referring to FIG. 3, tissue stress sensor 20 includes wafer 30 which has a nonresponsive portion 32 and a responsive portion (also denoted as a stress sensitive element, a diaphragm, or diaphragm portion) 34. Nonresponsive portion 32 serves mainly to support responsive portion 34. Under conditions when tissue stress sensor 20 is not being applied against tissue 24, radial artery 26' has a generally rounded opening (or lumen) as depicted at 26'. As wafer 30 of tissue stress sensor 20 is pressed against tissue 24, stress is created in tissue 24. This stress loads responsive portion 34 of wafer 30 thereby causing responsive portion 34 to deflect. In addition to causing the deflection of responsive portion 34, the stress created in tissue 24 also causes radial artery 26' to flatten (or applanate) along its top surface 36. As the blood pressure within radial artery 26 changes (i.e. pulsates), stress is created in tissue 24 which disturbs the equilibrium between responsive portion 34 of water 30 and top surface 28 of tissue 24. This disturbance in equilibrium causes movement between diaphragm 34 of wafer 30 and top surface 28 of overlying tissue 24. Such movement exists until a new equilibrium is established. The ability of diaphragm 34 to move and assume a unique displacement position for a given blood pressure within radial artery 26 forms the fundamental mechanism whereby tissue stress transducer 20 is capable of sensing the intra-arterial pressure of radial artery 26.

Because sensor 20 is used to compress or applanate radial artery 26 during blood pressure measurement, as well as measure the contact stress in tissue 24, the geometry of sensor 20 and its surrounding structure are vital to the proper conduction of stresses from radial artery 26 to tissue surface 28. A detailed discussion of sensor 20 and its associated structure now follows.

Figure 4:
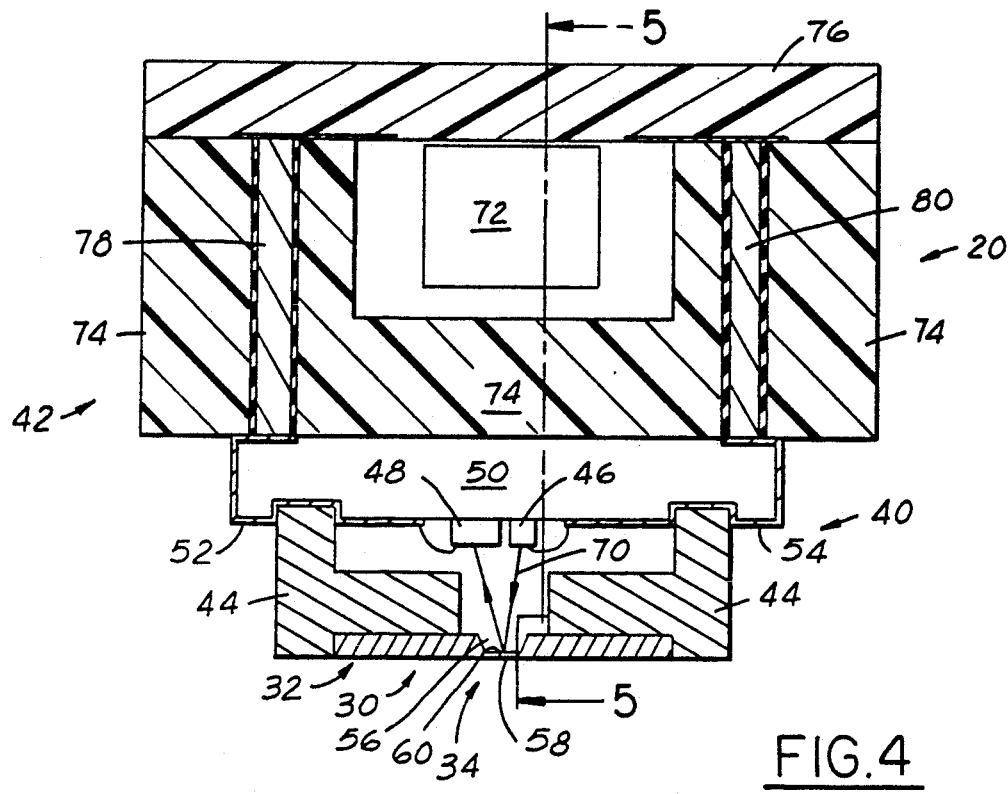
FIG. 4 is a cross sectional view of the tissue contact stress sensor of the present invention taken substantially along lines 4—4 of FIG. 3.

Now referring to FIG. 4, tissue contact stress sensor 20 is comprised of sensor head 40 and sensor base portion 42. Sensor head 40 comprises the transducer portion of sensor 20 and sensor base portion 42 includes electronic circuitry and other mechanical support structure necessary for properly operating sensor head 40. Sensor head 40 is generally comprised of six elements: sensor wafer 30, spacing structure 44, infrared emitting diodes (typified at 46), photo receivers (typified at 48), emitter/detector substrate 50 and circuit traces 52, 54.

An important feature of sensor 20 centers around the material and construction of sensor wafer 30. Sensor wafer 30 is formed from a wafer of single crystal silicon (SCS). Responsive diaphragm portion 34 of wafer 30 is formed by chemically micro-machining a trough 56 in the face of SCS wafer 30. This trough has a tetragonal-pyramidal geometry due to the crystal lattice structure of the SCS wafer 30. The bottom of the trough area 58 defines responsive diaphragm portion 34 of wafer 30. This portion defines a thin diaphragm region of highly controlled thickness and geometry. A major advantage in using SCS in the construction of diaphragm 34 is its superior engineering properties and its ability to be micro-machined which in turn provides a one-piece structure free of pre-stressing. Additional benefits in using SCS material include its ability to replicate small geometric features precisely and repeatedly, its linear elastic properties (i.e., almost no hysteresis) and its ability to quickly evidence its failed condition (under failure, the SCS diaphragm 34 totally fails thereby immediately evidencing its failed condition). This is to be contrasted with other materials which, under failure, do not fracture as does SCS but rather undergo inelastic deformation. Once the diaphragm undergoes inelastic deformation it loses its calibration but generally does not manifest its extreme, failed condition thereby usually going unnoticed.

Underside 60 of trough 56 is preferably metalized with a reflective material such as aluminum or gold. The thickness of the aluminum or gold is preferably generally 600 angstroms and its purpose will be explained shortly. Responsive portion 34 of wafer 30 changes its geometry with applied stress as a function of the material properties of the diaphragm. It is important to note that a coating of aluminum or gold generally 600 angstroms in thickness does not materially alter the properties of diaphragm portion 34 of wafer 30.

In the construction of tonometry sensors, the elasticity of responsive portion 34 of wafer 30 must be compatible with the characteristics of human tissue. If diaphragm surface 34 deforms excessively when responding to the stress of surface tissue 28, the tissue surface stress contour transduced by the sensor will be distorted, potentially affecting the accuracy of the measurement. Calculations, numerical simulation and experimental data have shown that diaphragm 34 of wafer 30 should be generally 50 times stiffer than that typical of tissue overlaying the artery of interest. The structural flexibility of the preferred embodiment is 0.24 microinch/mmHg measured at the midline of responsive diaphragm portion 34 of wafer 30.

Figures 6, 7A, 7B:
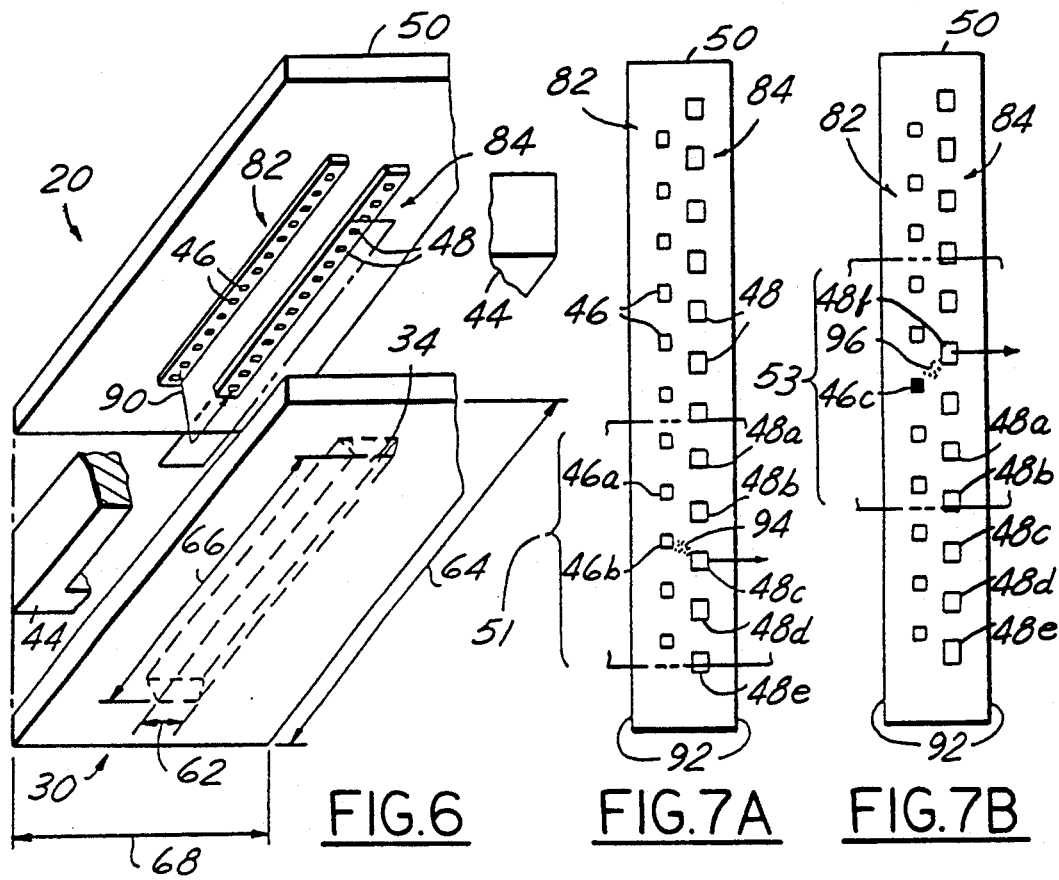
FIG. 6 is a partially exploded view of the tissue contact stress sensor of the present invention.
FIGS. 7A and 7B are diagrammatic views of the emitter and detector portions of the semiconductor assembly of the present invention.

Now referring of FIG. 4 and FIG. 6, width 62 of trough bottom 58 affects the maximum achievable spatial resolution and sensitivity. It has been empirically determined that width 62 is adequate for measurements in adult radial arteries when it is generally 0.020 inches. Narrower dimensions will generally be required for measurements in arteries smaller than adult radial arteries. The perimeter dimensions of wafer 30 play an important role in achieving accurate measurements. When used on an adult radial artery, the length 64 of wafer 30 must be sized so as to minimize interference with anatomical structures (e.g., the head of the radial bone laterally and medial radial tendon centrally) lying on either side of radial artery 26. Concurrently, length 66 of diaphragm 34 should be as long as possible in order to reduce sensitivity to lateral positioning and to allow measurement of contact stress in regions surrounding radial artery 26. It has been found that a wafer length 64 of generally 0.500 to 0.700 inches along with length 66 of diaphragm 34 being generally 0.35 to 0.45 inches is adequate to achieve these goals.

Choice of width 68 of wafer 30 affects the distribution of tissue forces. If width 68 is made too small, wafer 30 has a tendency to bend radial artery 26 at the perimeter of wafer 30 which in turn detrimentally affects the accuracy of the stress measurements. For the adult radial artery, a width 68 of generally 0.20 inches has been found suitable.

Spacing element 44 provides alignment and positioning of diaphragm 34 vis-a-vis array of emitters 46 and array of detectors 48. Spacing structure 44 is preferably manufactured from materials such as silicon nitride having a thermal coefficient of expansion similar to that of SCS (the preferred material to be used in the construction of wafer 30 and diaphragm 34). If a material is chosen for spacing structure 44 which does not have a similar thermal coefficient of expansion to that of SCS, the strains induced in diaphragm 34 would cause a small displacement in diaphragm 34 causing offset and sensitivity errors in the transduced signal.

Responsive portion 34 of wafer 30 provides a continuous mechanical displacement proportional to local surface tissue stress values. This displacement is sampled optically by an array of infrared emitting diodes (typified at 46) placed parallel to an array of photo detectors (typified at 48). Preferably, the photo detectors are either photo transistors or photo diodes. Diodes 46 receive their operational current through circuit traces typified at 54. Diodes 46 radiate electromagnetic energy 70 onto underside surface 60 of diaphragm 34. Electromagnetic energy 70 is reflected from underside 60 surface of trough 56 and falls upon photo receiver 48. Photo receiver 48 transduces electromagnetic radiation 70 into an electric photo current signal which flows through circuit traces typified at 52 and is delivered to converter/multiplexer circuit 72. Substrate 50 forms the structural foundation upon which diodes 46 and photo receiver 48 are constructed. Support structure 74 connects sensor head 40 and all of its component parts to interconnect PC board 76. Compression connectors 78, 80 provide a convenient way of delivering power from multiplexing and power circuits 102 to emitter array 46 within head 40 and delivering transduced signals from detector array 48 to amplifier circuits 100.

Figure 5:
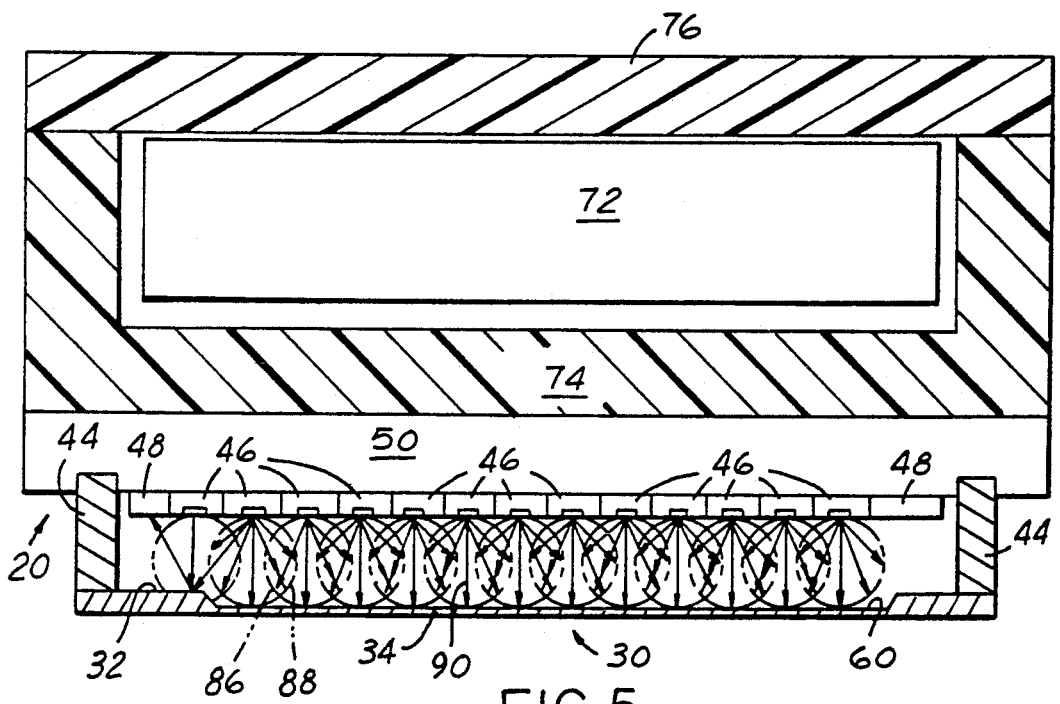
FIG. 5 is a cross-sectional view of the tissue contact stress sensor of the present invention taken substantially along lines 5—5 of FIG. 4.

Now referring to FIG. 5 and FIG. 6, sensor 20 of the present invention includes wafer 30, spacer 44 and emitter/detector substrate 50. Wafer 30 includes nonresponsive portion 32 and responsive portion 34. Responsive portion 34 provides a continuous mechanical displacement proportional to local surface tissue stress values. This displacement is sampled optically by array 84 of photo detectors placed parallel to array 82 of emitters. Array 82 is preferably constructed from a plurality of individual, infrared emitting diodes 46 and array 84 of photo detectors is comprised of a plurality of individual photo detectors 48. Photo detectors 48 are preferably photo transistors or photo diodes. The beam field associated with each infrared diode (typical beam fields for two adjacent photo diodes 46 shown at 86, 88) is arranged to overlap the beam field of adjacent diodes 46. This overlapping technique produces spatially sampled outputs, which are spatially smoothed, from each opto electronic channel. These outputs collectively represent a continuous, spatially weighted integral of the deflection of responsive portion 34 of wafer 30.

The fundamental advantage offered by the continuous diaphragm approach is its ability to monitor stress at any arbitrary location along its length and its inherent ability to spatially smooth the localized stress values. In addition to these advantages, the disclosed arrangement of emitter array 82 and sensor array 84 complements the diaphragm's properties by optically integrating the diaphragm's deformation over a finite region. Due to the overlapping beam fields 86, 88 of adjacent diodes 46, the measurement provided by each receiver 48 represents a spatially overlapping integral of the displacement of responsive portion 34 of wafer 30 in a region surrounding a diode/receiver pair. Preferably, a constant energy flux is radiated from each diode 46 with a Lambertian pattern (cosine law distribution) about an axis normal to the surface of each diode 46. A portion of this energy flux is reflected by the metalized coated underside 60 of responsive portion 34 of wafer 30 thereby striking one or more receivers 48 in the array of photo detectors 84. This in turn produces a photo current in each receiver 48 which is converted to a voltage by a current to voltage conversion circuit within converter/multiplexer circuit 72.

As diaphragm 34 responds to tissue stress, the electromagnetic radiation reflected from the active area of diaphragm 34 is dispersed. This action reduces the amount of radiation which would otherwise reach the neighboring receivers 48 and causes a reduction in their output signal. This dispersion of light rays 90 away from select receivers produces only a small deviation in the output signal of the select receivers (hereinafter referred to as the sensors inherent small signal current to total current ratio or small Isc/Itc ratio), and accordingly it is important to choose the geometric relationship of diode 46, receiver 48 and responsive portion 34 of wafer 30 to optimize the change of optical power received as a function of diaphragm displacement.

Although in the disclosed embodiments no device is shown disposed between diaphragm 34 and arrays 82, 84, it is contemplated that a device such as a lens or a mask, if so placed, may improve the sensors Isc/Itc ratio. For example, a thin opaque element (mask) could be placed between diaphragm 34 and arrays 82, 84 in a plane parallel to that of diaphragm 34. Windows could be placed through this element to allow energy from emitter array 82 to strike diaphragm 34 in a preferred region and be reflected to a preferred region of one (or more) detectors 48. To understand how the mask may improve the Isc/Itc ratio, it is helpful to first, consider how the unmasked version operates.

As the diaphragm bends, rays diverge away from select receivers 48 thereby reducing the amount of energy received as a function of the diaphragm curvature. In contrast, the mask could be designed so that as the diaphragm geometry (in the region where the beam strikes) changes with applied stress, the resulting reflected beam is partially blocked by the mask. This results in a more significant change in the amount of received energy per unit change in stress. The resulting improved Isc/Itc ratio improves signal quality and reduces the impact of thermal stresses and time degradation of the emitter and detector components.

As was mentioned above, even with the use of a mask, the inherent nature of the present invention limits the maximum achievable Isc/Itc ratio. Because of this fact, it is necessary to compensate for the variation in output signal caused by factors unrelated to blood pressure inasmuch as these factors could greatly compromise the accuracy of the system. Such factors may include the temperature dependence of the various optical and mechanical components which comprise sensor head 40, along with the variations experienced as the system ages. If these variables are not compensated for, unacceptable offset and gain errors could corrupt the accuracy of the sensor stress signal. To accomplish this compensation, one of the diode/receiver pairs are used to generate a reference signal by reflecting energy exclusively off nonresponsive portion 32 of diaphragm wafer 30. Inasmuch as this region is fixed, any variation in the photo current produced by the receiver 48 in this reference diode/receiver pair would be due to temperature, aging and environmental factors in array components 82, 84. This reference signal generated by reference receiver 48 is fed into the appropriate correction circuity (or software) which in turn performs the appropriate adjustment in the offset and gain and of each sensor channel as a function of the reference signal.

Now referring to FIGS. 7a and 7b, diode array 82 is arranged such that each diode 46 in the array of diodes 82 is generally arranged in a straight row substantially parallel to a long side 92 of electronic substrate 50. Likewise, each receiver 48 in the array of receivers 84 is generally arranged in a straight row which is substantially parallel to a long side 92 of electronic substrate 50. Row of diodes 46 is spaced apart from the row of receivers 48 and each diode 46 is juxtaposed with two receivers 48 such that it lies generally equidistant from its two closest receivers 48. This generally equidistant (or offset) relationship is demonstrated in FIG. 7a by virtue of emitter 46a being generally equidistant from its two closest detector neighbors 48a, 48b. Although this equidistant relationship has some advantages, which are discussed below, it is believed that other arrangements between emitters and detectors may also work effectively.

Coordination of the activation and monitoring of selected diode/receiver pairs together with the offset geometry between diodes 46 and receivers 48 allows a higher effective spatial resolution than can be achieved by using the same number of diode/receiver pairs which are horizontally matched in a one-to-one configuration across the entire length of electronic substrate 50. Due to the disclosed diagonal spacing of diode/receiver pairs, the effective spatial resolution of sensor 20 is effectively doubled in comparison to the resolution achievable using horizontally matched diode/receiver pairs. A similar approach could be used if the elements were aligned without offsetting; however, this would result in nonequal reflective angles and measurement regions being produced for alternate interrogation sites.

In the example shown in FIG. 7a, if an artery of interest (outlined at 51) spans receivers 48a–48e, it would be generally centered about location 94. One or more emitters within emitter array 82 may be used with one or more detectors within detector array 84 to form a select group of emitter/detectors for detecting tissue stress. Likewise, in reference to FIG. 7b, if the artery of interest (outlined at 53) appeared centered about location 96, one or more emitters may be used in conjunction with one or more detectors to detect tissue stress.

Figure 8:
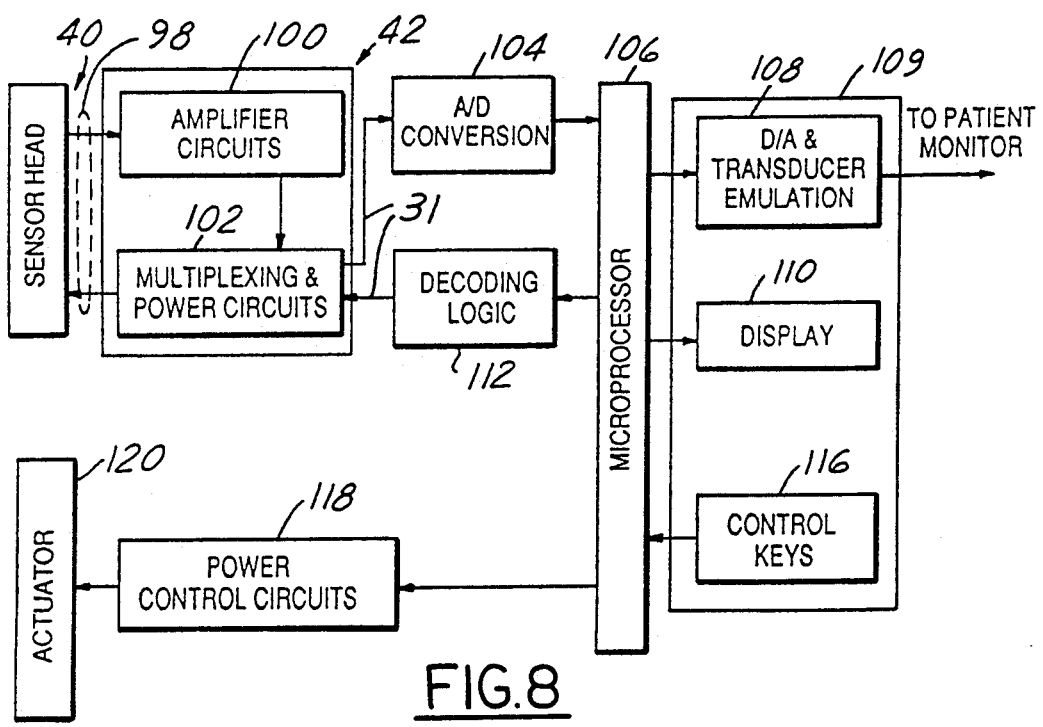
FIG. 8 is an electronic block diagram of the tissue contact stress sensor and associated supporting electronics of the present invention.

Now referring to the drawing of FIG. 8, sensor head 40 is electronically coupled via multiple communication lines 98 to sensor base portion 42. Sensor base portion 42 provides amplifier circuitry 100 to convert the current output signals from the array of detectors 84 to voltage output signals. These voltage signals are sent through multiplexer 102 where they are selectively digitized by A/D converter 104 and passed along to microprocessor 106. Microprocessor 106 performs the error correction spoken of earlier in the application and can also perform various other data compilation/analysis tasks. The blood pressure data can then be sent to any number of outputs such as a digital to analog converter 108 in cases where an analog representation of blood pressure is desirable. Blood pressure data may also be sent to display device 110 where it can provide the user with a continuously updated digital readout of blood pressure. Microprocessor 106 can be programmed to control decoding logic circuitry 112 which in turn activates select power circuits within multiplexing and power circuits 102.

The user of the system of the present invention can be given certain control options which can be input to microprocessor 106 via control keys 116. Power control circuit 118 can be used to interface microprocessor 106 to any number of mechanical actuators 120 which may be used to respond to various commands from microprocessor 106 in the utilization of sensor 40. For example, a routine may be used by microprocessor 106 which periodically queries whether sensor head 40 is properly applanating the artery of interest. If it is determined that the artery of interest is not properly applanated by wafer 30, microprocessor 106 may activate power control circuit 118 to command actuator 120 to move sensor 20 such that it properly applanates the artery of interest. Other applications may be devised where it is desirable to move, or otherwise control sensor head 20.

Figure 9:
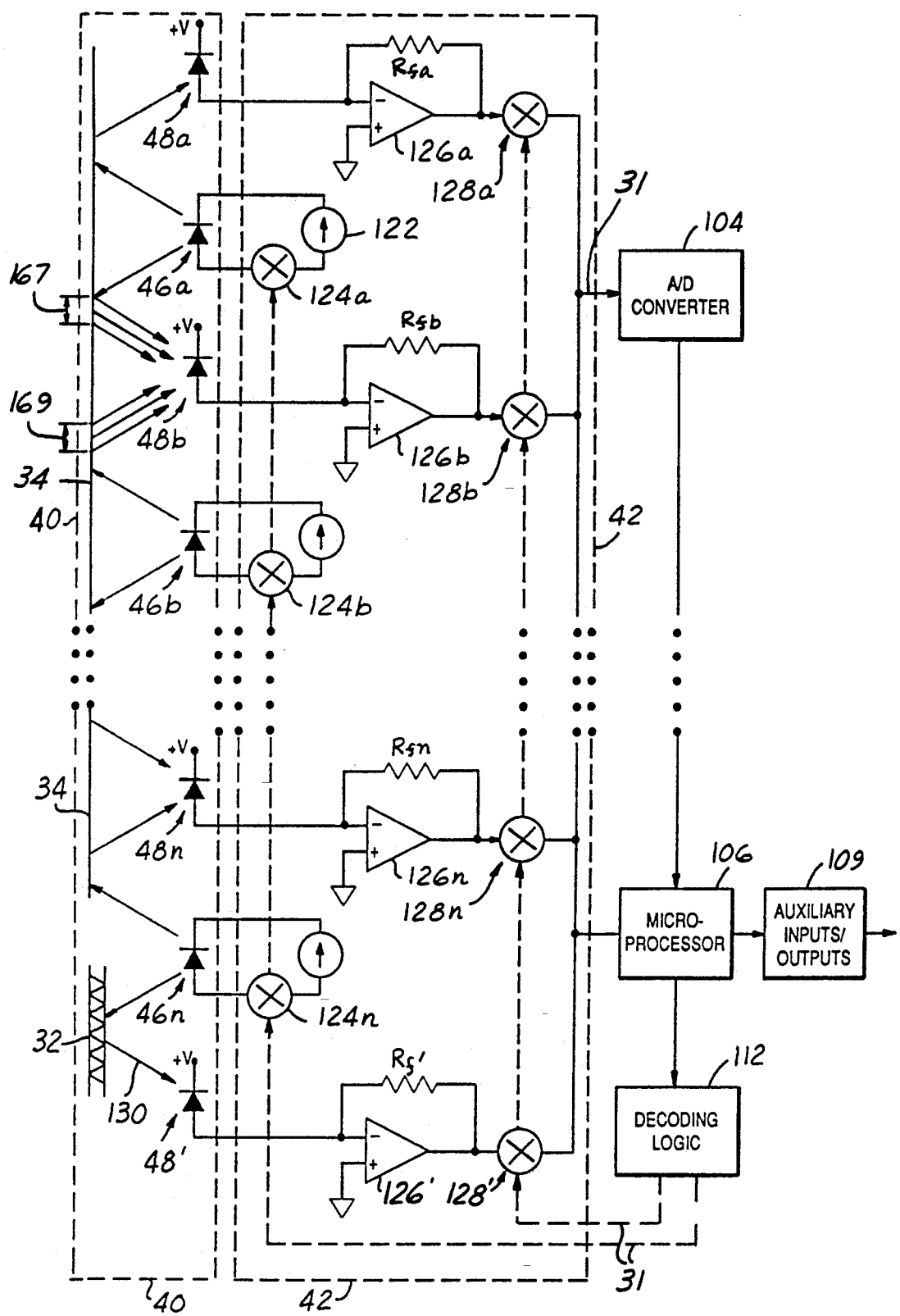
FIG. 9 is a detailed schematic of blocks 40 and 42 of FIG. 8.

Now referring to the drawing of FIG. 9, sensor head 40 is comprised of a continuous responsive diaphragm portion 34 which reflects light from diodes 46(a–n) and onto receivers 48(a–n). Each diode 46 is fed by current source typified at 122 which can be selectively switched on and off via a respective switch 124(a–n). These switches 124a through 124n are all individually controlled via decoding logic circuit 112. This is the fundamental mechanism whereby each diode 46a through 46n can be selectively activated to determine what portion of diaphragm 34 is best suited to be used to transduce the tissue stress signal. Each receiver 48a through 48n receives a portion of the light reflected from diaphragm 34 and converts this reflected light into an electrical current signal which is converted to a voltage by each receiver's respective converter 126a through 126n. Converters 126a through 126n are configured as current to voltage converters which effect a linear current-to-voltage conversion of the current signal derived from the respective receiver. Current-to-voltage converter circuits are well known to those skilled in the art and, accordingly, will not be discussed in detail here. The output of each converter is made available to its respective switch 128a through 128n. Switches 128a through 128n are controlled via decoding logic 112 which enables microprocessor 106 to select any output from converter 126a through 126n and place it on cable 31 where it is digitized by A/D converter 104.

One detector 48' is adapted to receive light 130 which is reflected from nonresponsive portion 32 of wafer 30. As has previously been discussed, detector 48' is used to generate a reference signal which will be used by microprocessor 106 to compensate for offset and gain errors due to temperature, aging and other environmental factors.

Figure 10:
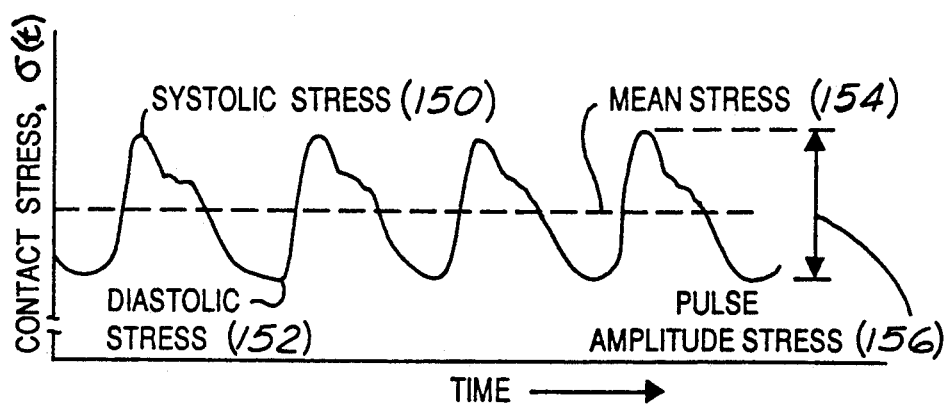
FIG. 10 is a graphic representation of a typical blood pressure waveform.
Figure 11:
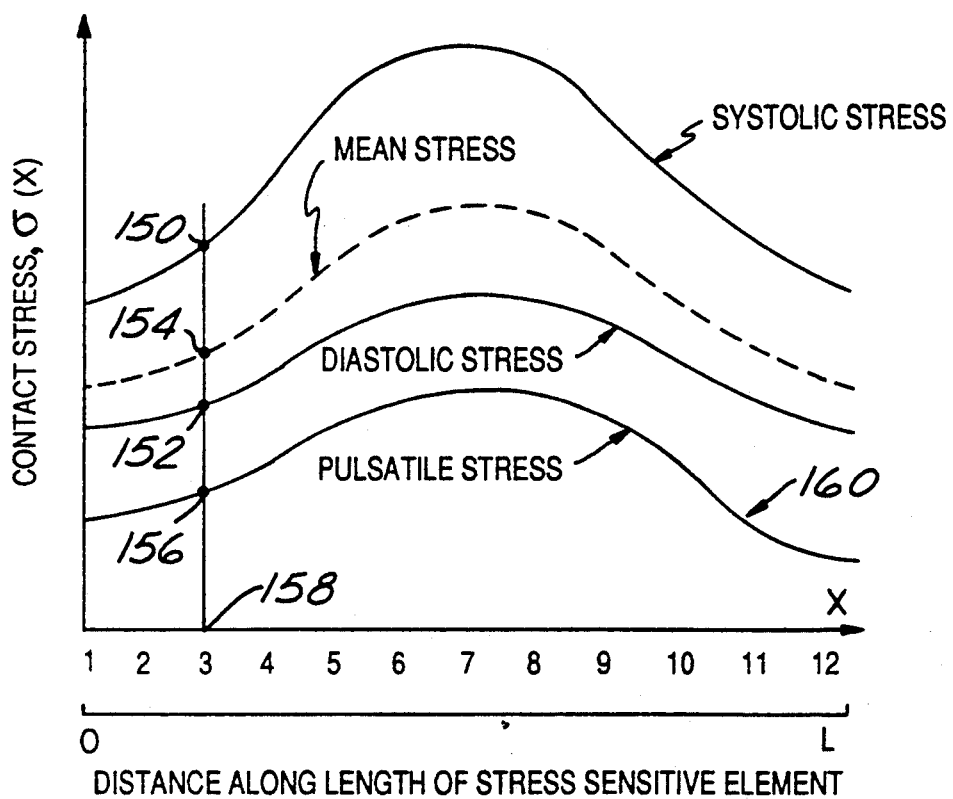
FIG. 11 is a graphical representation of contact stress versus distance along the length of a stress sensitive element.

Now referring to FIGS. 3, 5, 7A and 7B, and 9, when responsive portion 34 of wafer 30 (responsive portion 34 also known as tissue stress sensitive element 34) is placed against tissue 24, such that the artery of interest (outlined at 51 of FIG. 7A) is spanned by receivers 48a–48e, each receiver 48a–48e will generate a contact stress signal having the characteristic waveform shown in FIG. 10. Receivers which are close to center 94 of artery 51 will generate a characteristic waveform of greater magnitude than those at the peripheral edges of artery 51. The characteristic contour of the contact stress waveform generated by any one of the receivers 48a–48e will exhibit the following characteristics; a point of maximum (or systolic stress) 150 which corresponds to a peak or systolic blood pressure within artery 26, and a point of minimum (diastolic) stress 152 which corresponds to the diastolic blood pressure within artery 26. Mean stress 154 and pulse amplitude stress 156 are mathematically computed based on the following formulas:

$$\sigma_{mean} = \frac{\int_{t_1}^{t_1+\tau} \sigma(t) \cdot dt}{\int_{t_1}^{t_1+\tau} dt},$$

where $\tau$ = one heartbeat $\sigma_{pulse\ amplitude} = \sigma_{systolic} - \sigma_{diastolic}$ Now referring to FIGS. 10 and 11, although contact stress can be plotted as a function of time (as depicted in FIG. 10), it can also be plotted as a function of distance along the length of the stress sensitive element 34. For example, if the characteristic contact stress curve of FIG. 10 represented the output of photo receiver 48c (FIG. 7A), and photo receiver 48c was defined as the third receiver in the array 48 of photo receivers, the characteristic points of systolic stress 150, diastolic stress 152, mean stress 154, and pulse amplitude stress 156 of FIG. 10 would be plotted above position number 3 indicated by reference numeral 158 in FIG. 11. If the characteristic stress points from all of the 12 photo receivers within the array 48 of photo receivers are plotted, a curve resembling that of FIG. 11 will result. The stress information present in FIG. 11 is used in conjunction with the three methodologies set forth hereinafter to determine which portion along the stress sensitive element is best suited for determining the intra-arterial blood pressure of the artery of interest. These three methodologies will now be described in detail.

A. CONTACT STRESS ENERGY METHOD

The contact stress energy method is based upon the theory that the energy coupling between the artery of interest and the contact stress sensitive element is the greatest in the immediate vicinity of the artery of interest. Thus, one can determine the portion of the stress sensitive element which directly overlies the artery of interest by determining which portion of the stress sensitive element is in receipt of the maximum contact stress energy. This method uses the square of the contact stress values to obtain a measure of contact stress energy and thereby construct a relationship between contact stress energy and position along the length of the stress sensitive element. The centroid of the contact stress energy contour is calculated thereby yielding the location along the stress sensitive element which is used for determining intra-arterial blood pressure. In mathematical terms, the centroid of contact stress energy is calculated as follows:

$$\overline{X} = \frac{\int_b^c x \cdot E(x) \cdot dx}{\int_b^c E(x) \cdot dx} \quad (1)$$

where:
$\overline{X}$ = centroid of energy
$x$ = location along the length of the stress sensitive element
$E(x)$ = stress energy at location $x$
$b, c$ = limits of integration Wherein, contact stress energy $E(x)$ is computed as follows:

$$E(x) = (\sigma(x))^2 \quad (2)$$

where:
$E(x)$ = stress energy at location $x$
$\sigma(x)$ = stress datum sensed by stress sensitive element at location $x$ The above referenced methology is demonstrated graphically in FIG. 12. To implement the contact stress energy method, one first must select one of the stress contours as set out in FIG. 11. While any one of the four stress contours may perform satisfactorily when implementing the contact stress energy method, the pulsatile stress energy contour is preferred. Thus, after obtaining pulsatile stress values across the length of the stress sensitive element (as depicted in graph 160 of FIG. 11), each pulsatile stress value (exemplified at 156) is squared thereby relating contact stress energy $E(x)$ to the distance along the stress sensitive element. The centroid of the contact stress energy curve 162 is found by applying formula 1 as set out above.

Although the above method may appear similar to those methods set out in U.S. Pat. No. 4,802,488 and U.S. Pat. No. 4,893,631, those disclosed methods focus on the use of centroid of pressure—not centroid of energy. The difference between the centroid of energy approach and those methods set out in the '488 and '631 patents may be illustrated by a simple example. Assume that the pulsatile stress is sampled at five locations along a stress sensitive element [$p(x)$, $x = 1$ to 5]. If the values sampled at each of the five locations were as follows $p(1) = 10$, $p(2) = 20$, $p(3) = 50$, $p(4) = 30$, and $p(5) = 10$, the center of pressure would be found by the equation:

$$X_{cp} = \frac{\sum_1^5 (p(x) \cdot x)}{\sum_1^5 p(x)} = 3.08$$

Whereas the centroid of pulse energy is found by the equation:

$$X = \frac{\sum_1^5 (p(x)^2 \cdot x)}{\sum_1^5 p(x)^2} = 3.125$$

Thus, the above illustration shows that the contact stress energy method of determining which portion of a stress sensitive element is best suited for determining intra-arterial blood pressure is distinguishable in both methodology and results from previous approaches.

B. WEIGHTED CONTACT STRESS ENERGY METHOD

Similar to the method previously disclosed, this method uses the contact stress energy $E(x)$, but in addition attaches a "weighting function" to the contact stress energy contour. Weighting functions can be selected based on their ability to accentuate the influence of regions with greater pulse energy thus effectively "weighting" those higher energy locations to a greater degree. After defining $F[E(x)]$ as a weighted function of pulse energy, the effective center of the artery of interest is estimated as corresponding to the centroid of the weighted contact stress energy function over a selected energetic region of the stress sensitive element. This method is expressed mathematically as follows:

$$\overline{X} = \frac{\int_b^c x \cdot F[E(x)] \cdot dx}{\int_b^c F[E(x)] \cdot dx} \quad (3)$$

where:
$\overline{X}$ = centroid of energy
$x$ = location along the length of the stress sensitive element
$E(x)$ = stress energy at location $x$
$F[E(x)]$ = weighted function of stress energy
$b, c$ = limits of integration As disclosed earlier in conjunction with the first method, stress energy $E(x)$ is computed as follows:

$$E(x) = (\sigma(x))^2$$

where:
$E(x)$ = stress energy at location $x$
$\sigma(x)$ = stress datum sensed by stress sensitive element at location $x$ Although any number of weighting functions can be used, a preferred weighting function is defined as follows:

$$F[E(x)] = [E(x)]^N \quad (4)$$

where:
$F[E(x)]$ = weighted function of stress energy
$E(x)$ = stress energy at location $x$
$N$ = exponent of predetermined value The weighted contact stress energy method is graphically depicted in FIG. 13. When implementing this method, the following steps apply. First, a contact stress parameter (such as pulsatile stress) is measured at each location along the stress sensitive element. Then, each contact stress value is squared thereby converting it into contact stress energy and thereafter each energy value is operated on by a selected weighting function F[E(x)]. The centroid is then computed for this function over a selected energetic region of the diaphragm (i.e. b to c).

C. TISSUE FOUNDATION FLEXIBILITY METHOD

This method is used to determine the centroid of a tissue foundation flexibility profile. This concept is not based on the energy transfer theory but rather is based on the theory that the tissue immediately overlying the artery of interest is more flexible than the solid tissue remote from the artery of interest. When implementing this method, first the tissue foundation flexibility profile is defined, and then the centroid of that profile in the region of greatest tissue flexibility is calculated and used to define the effective center of the artery of interest. The tissue foundation flexibility profile is constructed using the following steps:

1. Applanating the artery of interest to a first applanation level and collecting a first set contact stress data (as set out in FIG. 11) across the length of the stress sensitive element.

2. Applanating the artery of interest to a second applanation level and collecting a second set of contact stress data across the length of the stress sensitive element. (Preferably, steps 1 and 2 collect diastolic stress data for the contact stress data during the two different applanation states.)

3. Computing the local tissue foundation modulus K(x) at locations x along the stress sensitive element. The local tissue foundation modulus K(x) at any location x is computed as follows:

$$K(x) = \frac{\sigma(x)_{AAS1} - \sigma(x)_{AAS2}}{AASI_1 - AASI_2} \quad (5)$$

where:
$\sigma(x)_{AAS1}$ = stress data sensed by stress sensitive element at location x while undergoing the first artery applanation state
$\sigma(x)_{AAS2}$ = stress data sensed by stress sensitive element at location x while undergoing the second artery applanation state
x = location along the length of the stress sensitive element
$AAS_1$ = First Artery Applanation State
$AAS_2$ = Second Artery Applanation State
$AASI_1$ = First Artery Applanation State Index
$AASI_2$ = Second Artery Applanation State Index 4. Computing the tissue foundation flexibility function C(x), wherein the tissue foundation flexibility function is calculated as follows:

$$C(x) = \frac{1}{K(x)} \quad (6)$$

5. Computing the centroid of the tissue foundation flexibility function for the regions of the stress sensitive element having the greatest flexibility, wherein the centroid of tissue foundation flexibility is computed as follows:

$$\overline{X} = \frac{\int_b^c x \cdot C(x) \cdot dx}{\int_b^c C(x) \cdot dx} \quad (7)$$

where:
$\overline{X}$ = centroid of tissue flexibility,
x = location along the length of the stress sensitive element
C(x) = tissue flexibility function (which is a measure of the flexibility of the tissue overlying said artery of interest) at location x
b, c = limits of integration The method of calculating the centroid of the tissue foundation flexibility function is graphically represented in FIG. 14. Because the centroid is computed in exactly the same way as the centroids in the previous two methods are calculated, further description is not necessary.

In determining the tissue flexibility function C(x), as disclosed above, it is necessary to compute the following function;

$$K(x) = \frac{\sigma(x)_{AAS1} - \sigma(x)_{AAS2}}{AASI_1 - AASI_2} \quad (8)$$

In calculating the tissue foundation modulus K(x), it is necessary to first calculate the first artery applanation state index $AASI_1$, and the second artery applanation state index $AASI_2$. A description of what those indexes are and how they may be calculated follows.

The artery applanation state indexes are a measure of artery applanation (or flattening) which occurs when the artery is acted upon by the stress sensitive element. Because it is impossible to directly measure the degree of artery flattening, indirect methods must be applied in assessing artery applanation. One such method is monitoring how much force is applied against the stress sensor as it is forced against the tissue overlying the artery of interest. For example, a force of 10 mmHg may receive an artery applanation index value of 1, 20 mmHg equals artery applanation index of 2, etc. Another method of deriving an artery applanation state index is simply to measure the linear movement of the stress sensitive transducer as it is displaced by the bellows 29 (see FIG. 2) or whatever actuating means is employed. Still other methods of determining an artery applanation state index include applanating an artery to a first state and then while held in that state, calculating the average contact stress across the entire length of the stress sensitive element. Mathematically, this method is expressed as follows:

$$AASI_1 = \sigma_{AVG(AAS1)} = \frac{\int_0^L \sigma(x)_{AAS1} \cdot dx}{\int_0^L dx}$$

where:
$\sigma_{AVG(AAS1)}$ = average stress value across the length of the stress sensitive element while the artery of interest undergoes the first artery applanation state
$AAS_1$ = First Artery Applanation State
$AASI_1$ = First Artery Applanation State Index $\sigma(x)_{AAS1}$ = stress data sensed by stress sensing element at location x while the artery of interest undergoes the first artery applanation state x = location along the length of stress sensitive element O, L = limits of integration across the length of stress sensitive element As seen earlier, contact stress $\sigma(x)$, can be represented by any one of the four stress parameters set out in FIG. 11. However, the preferred contact stress parameter when calculating tissue foundation modulus K(x) is diastolic contact stress.

D. WEIGHTED TISSUE FOUNDATION FLEXIBILITY METHOD

Just as the basic contact stress energy method was modified by applying a weighting function, the basic tissue foundation flexibility method can also be modified by applying a weighting function. Weighting functions are selected based upon their ability to accentuate the influence of regions with greater tissue flexibility thus effectively "weighting" those flexibile locations to a greater degree. F[C(x)] is defined as the weighted function of tissue flexibility, and the effective center of the artery of interest is estimated as corresponding to the centroid of the weighted tissue flexibility function over a selected energetic region of the stress sensitive element. This method is expressed mathematically as follows:

$$\overline{X} = \frac{\int_b^c x \cdot F[C(x)] \cdot dx}{\int_b^c F[C(x)] \cdot dx}$$

where:

$\overline{X}$ = centroid of tissue flexibility, x = location along the length of the stress sensitive element F[C(x)] = weighted tissue flexibility function (which is a weighted measure of the flexibility of the tissue overlying said artery of interest) at location x b, c = limits of integration The application of the weighted tissue flexibility method is analogous to that set out in conjunction with the weighted contact stress energy method. Accordingly, it is unnecessary to enumerate the details of applying such a method.

E. METHOD OF DETERMINING LIMITS OF CENTROID COMPUTATION

A common feature shared by each of the aforementioned four methodologies, is that they each compute the centroid of a function over predefined limits (b, c). This is in stark contrast with the approach of simply calculating the centroid over the full length of the stress sensitive element. The reason this approach is believed to be superior over that of simply calculating the centroid over the full length of the stress sensitive element is that it ignores those portions along the stress sensitive element which are distal from the artery of interest and therefore make only a minor contribution to the centroid of the function being examined. Accordingly, this approach eliminates from consideration portions of the function which are remote from the artery of interest thereby focusing on the portion which are proximate or centered above the artery of interest. Two methods will now be discussed, each of which can be used for determining the region (or regions) over which the centroid can be computed.

Percent of Maximum Method

Figure 12:
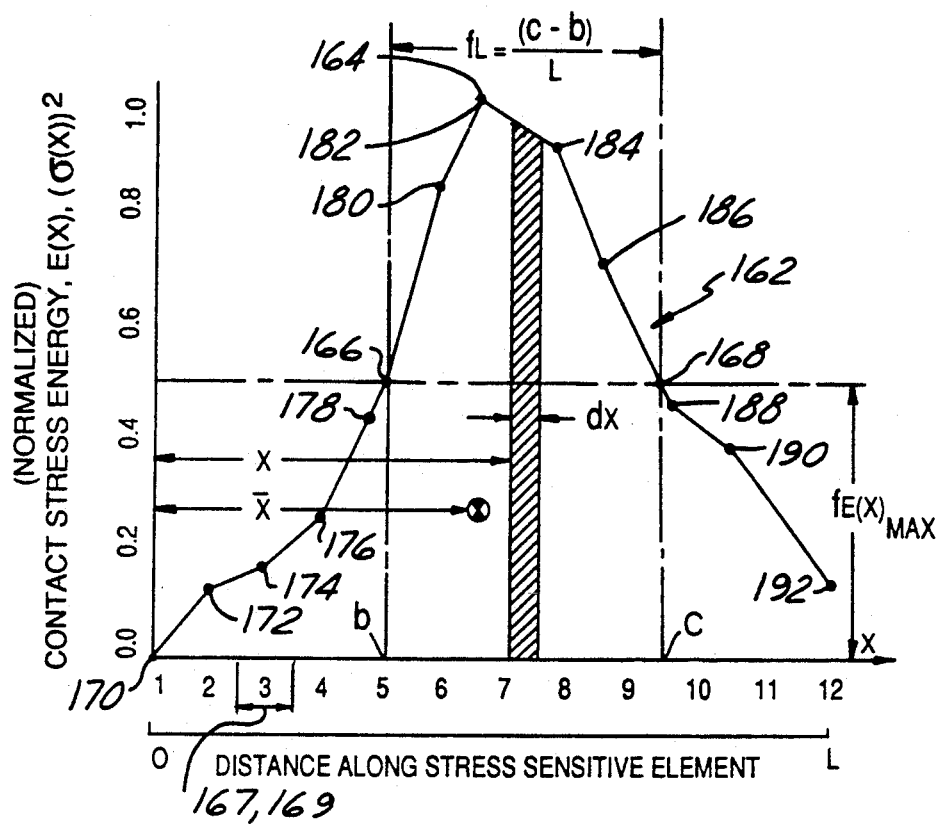
FIG. 12 is a graphical representation of a normalized contact stress energy curve plotted as a function of distance along the stress sensitive element.
Figure 13:
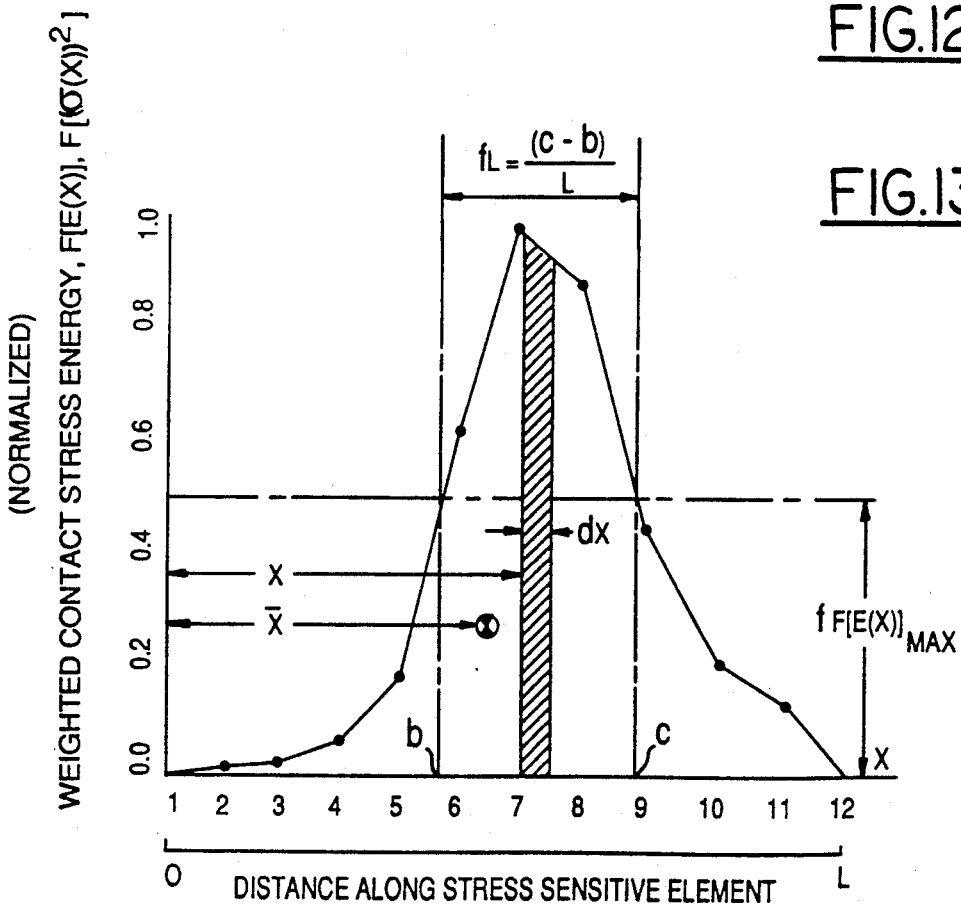
FIG. 13 is a graphical representation of a normalized weighted contact stress energy curve plotted as a function of distance long the stress sensitive element.
Figure 14:
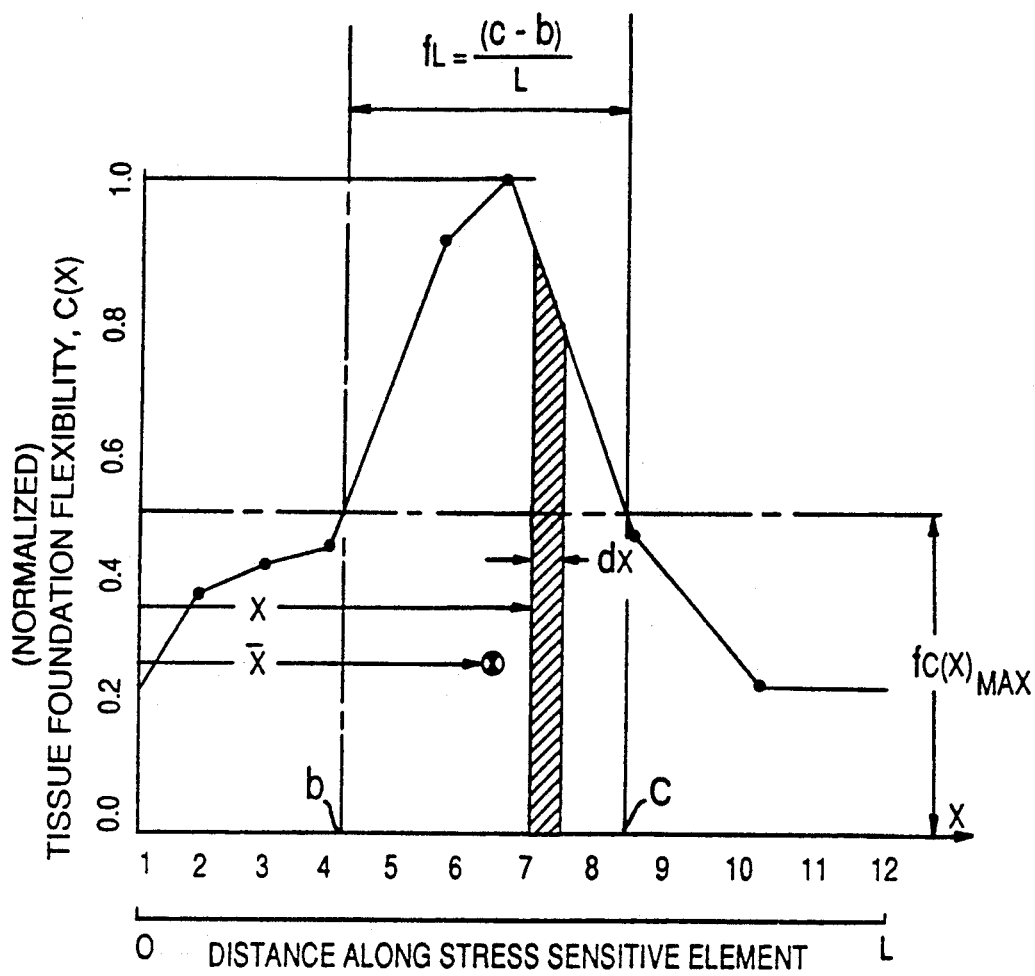
FIG. 14 is a graphical representation of a normalized tissue foundation flexibility curve plotted as a function of distance along the stress sensitive element.

The first method for determining the limits over which the centroid of a selected function will be computed, includes using only those regions of the select function which exceed an arbitrarily selected threshold fraction of the maximum value of the function. For example, applying this method to the contact stress energy function as set out in FIG. 12, first, maximum 164 is determined and then a predetermined portion of the maximum is taken. Suppose, for example, that fifty percent of maximum 164 will serve as the threshold fraction. This fraction intersects the contact stress energy function at points 166 and 168 thereby forming the limits (b, c) over which the centroid function will be calculated. This approach can be directly applied to the Weighted Contact Stress Energy Method of FIG. 13 and the Tissue Foundation Flexibility Function of FIG. 14. It is important to note that although the functions depicted in FIGS. 12, 13, and 14 are shown having only one contiguous region which satisfies the percent of maximum condition, it is probable that under actual use conditions, several discontiguous regions will satisfy the percent maximum condition. In this case, one would simply calculate a single centroid using those discontiguous regions of the energy curve which satisfy the percent of maximum condition.

Percent of Stress Sensitive Element Method

The second method of determining limits (b, c) includes using selected portions of greatest magnitude of the Contact Stress Energy Function, Weighted Contact Stress Energy Function, Tissue Foundation Flexibility Function, or Weighted Tissue Foundation Flexibility Function that have a cumulative total length equal to a predetermined percentage of the total length of the stress sensitive element. This method can be easily explained in conjunction with FIGS. 9 and 12. As seen in FIG. 9, sensing diode 48b is capable of sensing deflections along stress sensitive element 34 along regions or portions 167, 169 of stress sensitive element 34. Thus, when viewing point 174 of FIG. 12 (which we are assuming is the representative output of detector 48b), we see that this output does not represent a focused point along stress sensitive element 34, but rather represents the composit stresses sensed along continuous portions 167 and 169 of stress sensitive element 34. Accordingly, each output value 170 through 192 corresponds to one or more portions along stress sensitive element 34. Thus for example, in applying the present method of determining limits (b, c) from the contact stress energy function disclosed in FIG. 12, the following steps are preferred:

1. Ordering the contact stress energy values 170-192 according to magnitude,
2. Associating each of the contact energy stress values with a predetermined segment length, or lengths along the length of the stress sensitive element (e.g. stress value 174 is associated with lengths 167 and 169).
3. Selecting the contact stress energy values of greatest magnitude as previously ordered and totaling the lengths of each predetermined segment that is associated with the selected contact stress energy values.
4. Setting n equal to the number of contact stress energy values selected when the cumulative predetermined segment lengths (as totaled in step 3) exceed a predetermined percentage of the length of the stress sensitive element.
5. Computing the centroid of contact stress energy using only those n segments selected.

As disclosed in the Percent of Maximum Method, boundaries (b, c) may produce selected regions which are noncontiguous. Nonetheless, the disclosed method is applied identically regardless of whether the regions are contiguous or discontiguous.

F. METHOD OF DETERMINING PREDETERMINED VALUES USED IN THE DISCLOSED METHODOLOGIES

Many of the methodologies disclosed herein use predetermined values. For example, in utilizing the contact stress energy method, the limits of integration (b, c) are derived using a percent of maximum energy theory. Also disclosed is a second method of determining the limits of integration (b, c) by selecting those portions of greatest magnitude of the contact stress energy function, weighted contact stress energy function, tissue foundation flexibility function, or weighted tissue foundation flexibility function that have a cumulative total length equal to a predetermined percentage of the total length of the stress sensitive element. One preferred method of quantifying values to be used as predetermined percentages includes examining a large population of people including a diverse sampling of various groups of people such as males, females, adults, children, etc. and collecting therefrom blood pressure data both by way of tonometry and by way of invasive methods (or any other method which produces highly reliable test data to serve as a base reference). Once these two data bases have been gathered, various predetermined percentage values can be experimented with and the one or ones which produce the closest correlation to actual intra-arterial blood pressure are the ones which are selected for use in the disclosed methods.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. Accordingly, it is to be understood that the subject matter sought to be afforded protection hereby should be deemed to extend to the subject matter defined in the appended claims, including all fair equivalents thereof.

What is claimed is:

1. For use in a non-invasive blood pressure monitoring system, a method of determining which portion of a stress sensitive element of a tissue stress sensor is best located for detecting the stress of tissue overlying an artery of interest, said stress sensitive element having a length that exceeds a lumen of said artery of interest, said method including the steps of:
(A) placing said stress sensitive element of said tissue stress sensor in communication with said tissue overlying said artery of interest, and orienting said tissue stress sensitive element such that said tissue stress sensitive element spans beyond the lumen of said artery of interest;
(B) obtaining, from said tissue stress sensor, at least one electrical signal representing stress data across said length of said stress sensitive element, said stress data including a plurality of stress datum, each stress datum of said stress data representing stress communicated to a predetermined portion of said stress sensitive element from said tissue overlying said artery of interest, each said predetermined portion of said stress sensitive element lying along said length of said stress sensitive element;
(C) computing from said stress data, a centroid of energy associated with said stress sensitive element; and
(D) using said centroid of energy to determine which portion of said stress sensitive element is best located for determining the blood pressure within said artery of interest.

2. The method of claim 1 wherein, said stress data includes data corresponding to a systolic blood pressure within said artery of interest.

3. The method of claim 1 wherein, said stress data includes data corresponding to a diastolic blood pressure within said artery of interest.

4. The method of claim 1 wherein, said stress data includes data corresponding to a pulsatile blood pressure within said artery of interest.

5. The method of claim 1 wherein, said stress data includes data corresponding to a mean blood pressure within said artery of interest.

6. The method of claim 1, further including the step of:
(E) using each said stress datum value to calculate a corresponding energy value, each said energy value being associated with one of said predetermined portions of said stress sensitive element, and determining which one of said energy values is a maximum, and wherein step (C) further includes the sub-step of,
calculating said centroid of energy using only said stress datum values which have an energy value, as computed in step (E), which exceeds a predetermined percentage of said maximum energy value.

7. The method of claim 6, wherein said predetermined percentage is determined by assigning it a value equal to an empirically established percentage value that indicates a correlation between said centroid of energy and a center of said artery of interest.

8. The method of claim 1, wherein step (C) further includes the sub-steps of:
(i) using each said stress datum value to calculate a corresponding energy value, each said energy value being associated with one of said predetermined portions of said stress sensitive element;
(ii) ordering said energy values according to their respective magnitudes; and
(iii) calculating said centroid of energy by using only said stress datum values associated with a first n energy values of highest magnitude as ordered in sub-step 8(ii).

9. The method of claim 8, wherein n is determined by the sub-steps of:
(i) associating each said energy value ordered in sub-step 8(ii) with a predetermined segment length along the length of said stress sensitive element;
(ii) selecting said energy values of greatest magnitude as ordered in sub-step 8(ii), and totaling the predetermined segment lengths associated with all said selected energy values; and (iii) setting n equal to the number of energy values selected when the cumulative predetermined segment lengths as totalized in sub-step 9(ii) exceed a predetermined percentage of said length of said stress sensitive element.

10. The method of claim 9, wherein said predetermined percentage is determined by assigning it a value equal to an empirically established percentage value that indicates a correlation between said centroid of energy and a center of said artery of interest.

11. The method of claim 1, wherein step (C) further includes:
using each said stress datum value obtained in step (B) to calculate a corresponding energy value, each one of said energy values being associated with a predetermined portion of said stress sensitive element, and
generating a weighted energy value by attaching a weighting factor to each one of said energy values, and
calculating said centroid of energy, using said weighted energy values.

12. The method of claim 11, wherein step (C) further includes the steps of:
determining which one of said weighted energy values is a maximum, and
calculating said centroid of energy, using only said stress datum values which have a corresponding weighted energy value which exceeds a predetermined percentage of said maximum weighted energy value.

13. The method of claim 11, wherein step (C) further includes:
(i) ordering said weighted energy values according to their respective magnitudes; and
(ii) calculating said centroid of energy by using only said stress datum values associated with a first n weighted energy values of highest magnitude as ordered in sub-step 13(i).

14. The method of claim 13, wherein n is determined by the sub-steps of:
(i) selecting weighted energy values of greatest magnitude as ordered in sub-step 13(i) and totaling a cumulative length of each said predetermined segment associated with all said selected weighted energy values; and
(ii) setting n equal to a value equal to a total number of weighted energy values selected when the cumulative length as totalized in sub-step 14(i) equals said predetermined percentage of said length of said stress sensitive element.

15. The method of claim 11, wherein said centroid of energy is conducted as follows:

$$X = \frac{\int_b^c x \cdot E(x) \cdot dx}{\int_b^c E(x) \cdot dx}$$

where:
$\overline{X}$ = centroid of energy;
x = location along the length of the stress sensitive element;
E(x) = stress energy at location x;

F[E(x)] = weighted function of stress energy; and
b,c = limits of integration in the range of zero to L, where L is the length of the stress sensitive element.

16. The method of claim 15, wherein said stress energy E(x) is computed as follows:

$$E(x) = (\sigma(x))^2$$

where:
$\sigma(x)$ = stress datum sensed by stress sensitive element at location x.

17. The method of claim 16, wherein said weighted function of stress energy F[E(x)] is computed as follows:

$$F[E(x)] = [E(x)]^N$$

where:
F[E(x)] = weighted function of stress energy;
N = exponent of predetermined value.

18. The method of claim 17, wherein said stress datum $\sigma(x)$, includes datum corresponding to at least one of a diastolic blood pressure (x), a systolic blood pressure (x), a pulsatile blood pressure (x), and a mean blood pressure (x) within said artery of interest.

19. The method of claim 1, wherein step (C) includes computing said centroid of energy as follows:

$$\overline{X} = \frac{\int_b^c x \cdot E(x) \cdot dx}{\int_b^c E(x) \cdot dx}$$

where:
$\overline{X}$ = centroid of energy;
x = location along the length of the stress sensitive element;
E(x) = stress energy at location x; and
b,c = limits of integration in the range of zero to L, where L is the length of the stress sensitive element.

20. The method of claim 19, wherein said stress energy E(x) is computed as follows:

$$E(x) = (\sigma(x))^2$$

where:
$\sigma(x)$ = stress datum sensed by stress sensitive element at location x.

21. The method of claim 20, wherein said stress datum $\sigma(x)$, includes datum corresponding to at least one of a diastolic blood pressure (x), a systolic blood pressure (x), a pulsatile blood pressure (x), and a mean blood pressure (x) within said artery of interest.

22. For use in a non-invasive blood pressure monitoring system, a method of determining which portion of a stress sensitive element of a tissue stress sensor is best located along a length of said stress sensitive element for detecting a stress of tissue overlying an artery of interest, said length of said stress sensitive element exceeding the lumen of said artery of interest, said method including the steps of:
(A) placing said stress sensitive element of said tissue stress sensor in communication with said tissue overlying said artery of interest, and orienting said stress sensitive element such that said stress sensitive element spans beyond the lumen of said artery of interest;

(B) causing said stress sensitive element to act against said tissue overlying said artery of interest thereby causing in said artery, a first artery applanation state, and obtaining a first artery applanation state index;

(C) obtaining, during said first artery applanation state from said tissue stress sensor, at least one electrical signal representing a first set of stress data across said length of said stress sensitive element, said first set of stress data representing a plurality of stress datum, each said stress datum representing stress communicated to one of a plurality of portions of said stress sensitive element from said tissue overlying said artery of interest, said portions of said stress sensitive element lying along said length of said stress sensitive element;

(D) causing said stress sensitive element to act against said tissue overlying said artery of interest thereby causing in said artery, a second artery applanation state, and obtaining a second artery applanation state index;

(E) obtaining, during said second artery applanation state from said tissue stress sensor, at least one electrical signal representing a second set of stress data across said length of said stress sensitive element, said second set of stress data representing a plurality of stress datum, each stress datum representing stress communicated to one of said portions of said stress sensitive element from said tissue overlying said artery of interest;

(F) using said first and second sets of stress data and said first and second artery applanation state indexes to construct tissue flexibility data values which define a tissue flexibility function relating the flexibility to x, where flexibility is the flexibility of said tissue overlying said artery of interest and x is a location along said length of said stress sensitive element;

(G) computing, using said tissue flexibility data values, a centroid of tissue flexibility; and (H) using said centroid of tissue flexibility to determine which portion of said stress sensitive element is best located for determining the blood pressure within said artery of interest.

23. The method of claim 22, wherein said first and second sets of stress data includes data corresponding to a diastolic blood pressure within said artery of interest.

24. The method of claim 22, wherein said first and second sets of stress data includes data corresponding to a systolic blood pressure within said artery of interest.

25. The method of claim 22, wherein said first and second sets of stress data includes data corresponding to a pulsatile blood pressure within said artery of interest.

26. The method of claim 22, wherein said first and second sets of stress data includes data corresponding to a mean blood pressure within said artery of interest.

27. The method of claim 22, further comprising the step of:

(I) determining which of said tissue flexibility data values is a maximum, and wherein step (G) further includes the sub-step of, (i) calculating said centroid of tissue flexibility using only the tissue flexibility data values which have a magnitude which exceeds a predetermined percentage of said maximum tissue flexibility value.

28. The method of claim 27, wherein said predetermined percentage is determined by empirically establishing a percentage value that indicates a correlation between said centroid of energy and a center of said artery of interest.

29. The method of claim 22, wherein step (G) further includes the sub-steps of:

(i) ordering the tissue flexibility data values according to magnitude, and (ii) calculating said centroid of tissue flexibility by using only a first n of said tissue flexibility data values of highest magnitude as ordered in sub-step 29(i).

30. The method of claim 29, wherein said n is determined by the sub-steps of:

(i) associating each said tissue flexibility data value ordered in sub-step 30(i) with a predetermined segment length along said length of said stress sensitive element, (ii) selecting said tissue flexibility data values of greatest magnitude as ordered in sub-step 30(i) and totaling the lengths of each predetermined segment which is associated with a selected tissue flexibility data value, and (iii) setting said n equal to a number of tissue flexibility data values selected when the cumulative length of said selected segment lengths, as totalized in sub-step 30(ii), equals a predetermined percentage of said length of said stress sensitive element.

31. The method of claim 30, wherein said predetermined percentage is determined by empirically establishing a percentage value that indicates a correlation between said centroid of tissue flexibility and a center of said artery of interest.

32. The method of claim 22, wherein the centroid of tissue flexibility is computed as follows:

$$\overline{X} = \frac{\int_b^c x \cdot C(x) \cdot dx}{\int_b^c C(x) \cdot dx}$$

where:

$\overline{X}$ = centroid of tissue flexibility;

x = location along the length of the stress sensitive element;

C(x) = tissue flexibility function (which is a measure of the flexibility of the tissue overlying said artery of interest) at location x; and b,c = limits of integration in the range of zero to L, where L is the length of the stress sensitive element.

33. The method of claim 32, wherein computing said tissue flexibility function C(x), includes:

$$C(x) = \frac{1}{K(x)}$$

where:

K(x) = tissue foundation modulus and wherein, K(x) is computed as follows:

$$K(x) = \frac{\sigma(x)_{AAS1} - \sigma(x)_{AAS2}}{AASI_1 - AASI_2}$$

where:

$\sigma(x)_{AAS1}$ = stress data sensed by stress sensitive element at location x while undergoing the first artery applanation state;

$\sigma(x)_{AAS2}$ = stress data sensed by stress sensitive element at location x while undergoing the second artery applanation state;

x = location along the length of the stress sensitive element;

$AAS_1$ = First Artery Applanation State;

$AAS_2$ = Second Artery Applanation State;

$AASI_1$ = First Artery Applanation State Index; and $AASI_2$ = Second Artery Applanation State Index.

34. The method of claim 33, wherein said stress data $\sigma(x)$, includes data corresponding to one of a diastolic blood pressure (x), systolic blood pressure (x), a pulsatile blood pressure (x), and a mean blood pressure (x) within said artery of interest.

35. The method of claim 33, wherein calculating said first artery applanation state index $AASI_1$, includes applanating said artery of interest to a first artery applanation state $AAS_1$, and calculating an average stress data value $\sigma_{AVG(AAS1)}$, wherein $\sigma_{AVG(AAS1)}$ is calculated as follows:

$$AASI_1 = \sigma_{AVG(AAS1)} = \frac{\int_O^L \sigma(x)_{AAS1} \cdot dx}{\int_O^L dx}$$

where:

$\sigma_{ANG(AAS1)}$ = average stress value across the length of the stress sensitive element while the artery of interest undergoes the first artery applanation state;

O, L = limits of integration (across the length of stress sensitive element).

36. The method of claim 35, wherein said stress data $\sigma(x)_{AAS1}$, includes data corresponding to one of a diastolic blood pressure (x), systolic blood pressure (x), a pulsatile blood pressure (x), and a mean blood pressure (x) within said artery of interest.

37. The method of claim 33, wherein calculating said second artery applanation state index $AASI_2$, includes applanating said artery of interest to a second artery applanation state $AAS_2$, and calculating an average stress data value $\sigma_{AVG(AAS2)}$, wherein $\sigma_{AVG(AAS2)}$ is calculated as follows:

$$AASI_2 = \sigma_{AVG(AAS2)} = \frac{\int_O^L \sigma(x)_{AAS2} \cdot dx}{\int_O^L dx}$$

where:

$\sigma_{AVG(AAS2)}$ = average stress value across the length of the stress sensitive element while the artery of interest undergoes the second artery applanation state; and O, L = limits of integration (across the length of stress sensitive element).

38. The method of claim 37, wherein said stress data $\sigma(x)_{AAS2}$, includes data corresponding to one of a diastolic blood pressure (x), systolic blood pressure (x), a pulsatile blood pressure (x), and a mean blood pressure (x) within said artery of interest.

39. The method of claim 22 wherein step (G) further includes attaching a weighting factor to said tissue flexibility data values and computing said centroid of tissue flexibility, using said weighted tissue flexibility data values.

* * * * *

UNITED STATES PATENT AND TRADEMARK OFFICE
CERTIFICATE OF CORRECTION

PATENT NO. : 5,263,484
DATED : November 23, 1993
INVENTOR(S) : Martin et al It is certified that error appears in the above-identified patent and that said Letters Patent is hereby corrected as shown below:

At line 1 of column 26 of the patent, "σANG(AAS$_1$)" should be replaced with "σAVG(AAS$_1$)".

At line 60, column 21 of claim 15 of the patent, the formula should read as follows:

$$X = \frac{\int_b^c x \cdot F[E(x)] \cdot dx}{\int_b^c F[E(x)] \cdot dx}$$

Signed and Sealed this

Twelfth Day of July, 1994

Attest:

BRUCE LEHMAN

Attesting Officer        Commissioner of Patents and Trademarks